(12) United States Patent
Yang et al.

(10) Patent No.: US 7,666,890 B2
(45) Date of Patent: Feb. 23, 2010

(54) SYNTHESIS AND HERBICIDAL ACTIVITY OF 1- (2-SUBSTITUTED BENZO[D]THIAZOL-5-YL)-1H-1,2,4-TRIAZOL-5(4H)- ONE DERIVATIVES

(75) Inventors: Guangfu Yang, Wuhan (CN); Yanping Luo, Wuhan (CN); Zuming Liu, Wuhan (CN)

(73) Assignee: Huazhong Normal University, Wuhan (CN)

( * ) Notice: Subject to any disclaimer, the term of this patent is extended or adjusted under 35 U.S.C. 154(b) by 1 day.

(21) Appl. No.: 12/326,180

(22) Filed: Dec. 2, 2008

(65) Prior Publication Data

US 2009/0143229 A1  Jun. 4, 2009

Related U.S. Application Data

(63) Continuation of application No. PCT/CN2007/001134, filed on Apr. 9, 2007.

(51) Int. Cl.
*A61K 31/4196* (2006.01)
*C07D 249/08* (2006.01)

(52) U.S. Cl. .................. 514/383; 548/262.2; 548/266.2
(58) Field of Classification Search ............. 548/262.2; 514/383

See application file for complete search history.

(56) References Cited

U.S. PATENT DOCUMENTS 5,728,651 A * 3/1998 Hong et al. ................. 504/246

* cited by examiner

*Primary Examiner*—Kamal A Saeed
*Assistant Examiner*—Michael Barker
(74) *Attorney, Agent, or Firm*—Matthias Scholl P.C.; Matthias Scholl

(57) ABSTRACT

Synthesis and herbicidal activity of novel 1-(2-substituted benzo[d]thiazol-5-yl)-1H-1,2,4-triazol-5(4H)-one derivatives. Using a dose of 300 gai./h, the compounds of the invention possess significant herbicidal activity for *Echinochloa crusgalli, Digiatria sanguinalis, Setaria viridis, Brassica juncea, Amaranthus retroflexus* and *Chenopodium album.*

15 Claims, No Drawings

SYNTHESIS AND HERBICIDAL ACTIVITY OF 1- (2-SUBSTITUTED BENZO[D]THIAZOL-5-YL)-1H-1,2,4-TRIAZOL-5(4H)- ONE DERIVATIVES

CROSS-REFERENCE TO RELATED APPLICATIONS

This application is a continuation of International Patent Application No. PCT/CN2007/001134, with an international filing date of Apr. 9, 2007, designating the United States, now pending, which is based on China Patent Application No. 200610019345.7, filed Jun. 13, 2006. The contents of these specifications, including any intervening amendments thereto, are incorporated herein by reference.

BACKGROUND OF THE INVENTION

1. Field of the Invention

The invention relates to synthesis and herbicidal activity of 1-(2-substituted benzo[d]thiazol-5-yl)-1H-1,2,4-triazol-5(4H)-one derivatives.

2. Description of the Related Art

Over the past ten years, herbicide research related to protoporphyrinogen oxidase (protox) has been on the increase. Protox is as an enzyme that is responsible for conversion of protoporphyrinogen IX to protoporphyrin IX during production of chlorophyll. A protox inhibitor inhibits protoporphyrinogen oxidase, and causes protoporphyrin IX to accumulate in the cytoplasm and to generate singlet oxygen under the action of light and oxygen. Under the action of singlet oxygen on membrane lipids, cell membrane disassociates and cell endogens leak, resulting in cell death.

1,2,4-triazolinone derivatives are an example of protox inhibitors that have a widespread herbicidal activity In the contemporary herbicides research area, they become one of the most popular topics. In particular, sulfentrazone and carfentrazon-ethyl were developed by FMC, and azafenidin was developed by DuPont. However, much opportunity still exists in the development of advanced protox inhibitors.

BRIEF SUMMARY OF THE INVENTION

The invention, in its embodiments, uses a method of connecting benzothiazole groups having biological activity with 1,2,4-triazolinone, or modifying the structure of 1,2,4-triazolinone to design and synthesize novel 1,2,4-triazolinone derivatives.

In particular, it is one objective of the invention to provide 1-(2-substituted benzo[d]thiazol-5-yl)-1H-1,2,4-triazol-5(4H)-one derivatives having herbicidal activity.

It is another objective of the invention to provide a method of preparing 1-(2-substituted benzo[d]thiazol-5-yl)-1H-1,2,4-triazol-5(4H)-one derivatives having herbicidal activity.

In order to achieve the above objectives, in accordance with one embodiment of the invention, provided is a 1-(2-substituted benzo[d]thiazol-5-yl)-1H-1,2,4-triazol-5(4H)-one derivative represented by the general formula I:

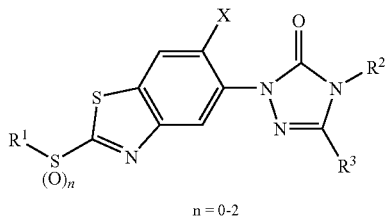

n = 0-2 wherein X represents F, Cl or Br; n is 0, 1 or 2; $R^1$ represents alkyl, substituted alkyl, haloalkyl, alkenyl, alkynyl, alkynylalkyl, carboxylic acid ester radical, dialkyl ether radical, benzyl, substituted benzyl, halobenzyl, or substituted aromatic heterocyclic methyl; $R^2$ represents methyl or difluoromethyl; and $R^3$ represents methyl or trifluoromethyl.

The 1,2,4-triazolinone derivatives represented by the general formula I are divided into the following two types according to the value of n. Particularly, for n equal to 0, the general formula I represents a compound represented by formula I-1, and for n equal to 1 or 2, the general formula I represents a compound represented by formula I-2.

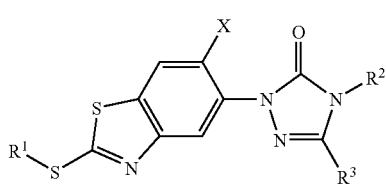

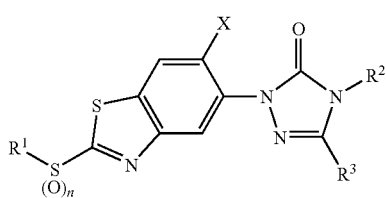

n = 1, 2

The definitions of X, $R^1$, $R^2$ and $R^3$ is the same for general formulae I-1 and I-2, as those for the general formula I.

This invention provides two methods for preparing the 1,2,4-triazol-3(4H)-one derivative represented by the general formula I, method A and method B, depending on the value of n.

Method A (for n=0): A method for preparing compound of formula I-1 comprises contacting compound represented by the general formula II with a compound represented by the general formula III, according to the following equation.

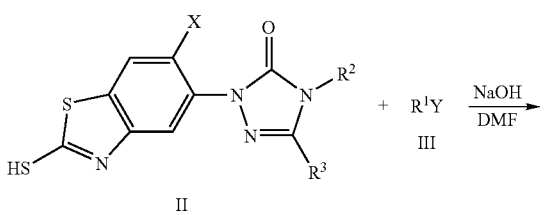

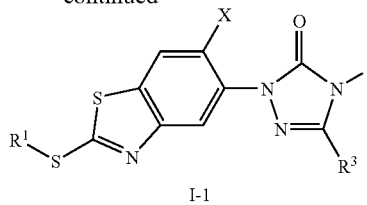

I-1 wherein X represents F, Cl or Br; Y represents Cl or Br; $R^1$ represents alkyl, substituted alkyl, haloalkyl, alkenyl, alkynyl, alkynylalkyl, carboxylic acid ester radical, dialkyl ether radical, benzyl, substituted benzyl, halobenzyl, or substituted aromatic heterocyclic methyl; $R^2$ represents methyl or difluoromethyl; and $R^3$ represents methyl or trifluoromethyl.

In the above reaction, a good yield can be obtained if the molar ratio of the compound of the formula II to the compound of the formula III to sodium hydroxide is about 1:1.1:1.2, a mixture of water and N,N-dimethylformamide is used as solvent, the volume ratio of water to N,N-dimethylformamide being 5:1, the reaction temperature is 25° C., and the reaction time is 2-6 hours.

Method B (for n=1 or 2): A method for preparing a compound of formula 1-2 comprises oxidizing a compound represented by the general formula I-1 with m-chloroperoxybenzoic acid (MCPBA), according to the following equation.

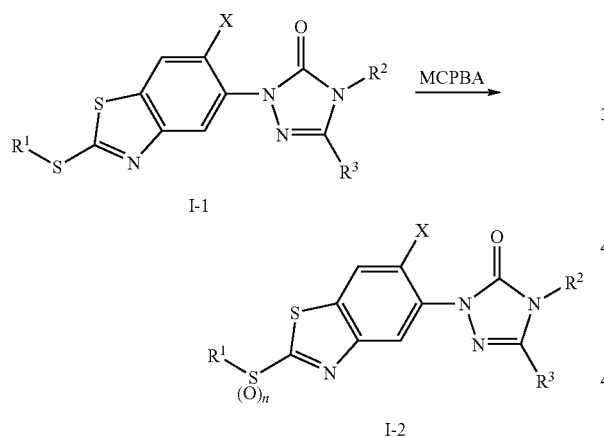

wherein X represents F, Cl or Br; n is equal 1 or 2; $R^1$ represents alkyl, substituted alkyl, haloalkyl, alkenyl, alkynyl, alkynylalkyl, carboxylic acid ester radical, dialkyl ether radical, benzyl, substituted benzyl, halobenzyl, or substituted aromatic heterocyclic methyl; $R^2$ represents methyl or difluoromethyl; and $R^3$ represents methyl or trifluoromethyl.

In the above reaction, the molar ratio of compound I-1 to m-chloroperoxybenzoic acid is 1:1 or 1:2, dichloromethane is used as reaction solvent, the reaction temperature is 0-25° C., and the reaction time is 2-4 hours. When the molar ratio of compound I-1 to m-chloroperoxybenzoic acid is 1:1, a compound of the formula I-2 is obtained, wherein n=1. When the molar ratio of compound I-1 to m-chloroperoxybenzoic acid is 1:2, a compound of the formula I-2 is obtained, wherein n=2.

The compound represented by the general formula II is an intermediate in the synthesis of a compound of the general formula I. A method for preparing a compound represented by the general formula II comprises contacting a compound represented by the general formula IV with potassium ethyl xanthogenate in N,N-dimethylformamide (DMF), according to the following equation.

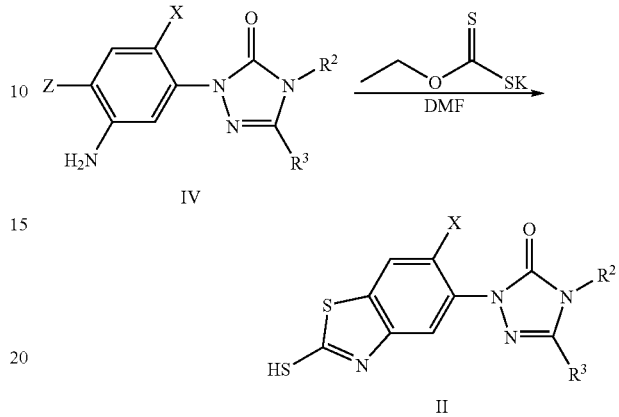

wherein X represents F, Cl, or Br; Z represents F, Cl, or Br; $R^2$ represents methyl or difluoromethyl; and $R^3$ represents methyl or trifluoromethyl.

In the above reaction, a good yield can be obtained if the molar ratio of the compound of the formula IV to potassium ethyl xanthogenate is about 1:2; N,N-dimethylformamide is used as solvent; reaction temperature is 140° C.; and the reaction time is 5-7 hours.

The compound represented by formula I features significant herbicidal activity for barnyard grass, common crabgrass, green bristlegrass, mustard, amaranthus retroflexus, and small goosefoot.

DETAILED DESCRIPTION OF THE INVENTION

EXAMPLES

Example 1

Preparation of 1-(6-chloro-2-mercaptobenzo[d]thiazol-5-yl)-4-(difluoromethyl)-3-methyl-1H-1,2,4-triazol-5(4H)-one

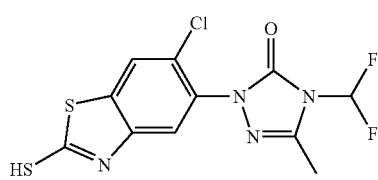

30 mL N,N-dimethylformamide was charged with 0.01 mol 1-(5-amino-2,4-dichlorophenyl)-4-(difluoromethyl)-3-methyl-1H-1,2,4-triazol-5(4H)-one. The mixture was stirred until it became clear. Then, 0.02 mol potassium ethyl xanthogenate was added to the mixture in two portions. The mixture was refluxed at 140° C. for 5 h, cooled, and poured into 100 mL ice water. Then, the mixture was acidified with 6 mol/L hydrochloric acid, and a large amount of solids crushed out.

The title compound was obtained in a 68% yield as a white solid after filtration.

M.p. 201-203° C.

Anal. Calcd for $C_{11}H_7ClF_2N_4OS_2$: C, 37.88; H, 2.02; N, 16.06; S, 18.39. Found: C, 37.57; H, 1.96; N, 16.30, S, 18.85.

$^1$H NMR (CDCl$_3$, δ/ppm): 2.515 (s, 3H, CH$_3$), 6.962-7.252 (t, 1H, CH, J=58 Hz), 7.263-7.535 (m, 2H, ArH), 11.033 (s, 1H, SH).

MS (m/z): 354.1 (M$^+$, 100), 355.8 (M+2, 25.16), 291.5 (48.58), 172.2 (35.66), 145.8 (58.61), 124.7 (57.77), 89.2 (55.89).

Example 2

Preparation of 1-(6-fluoro-2-mercaptobenzo[d]thiazol-5-yl)-4-(difluoromethyl)-3-methyl-1H-1,2,4-triazol-5(4H)-one

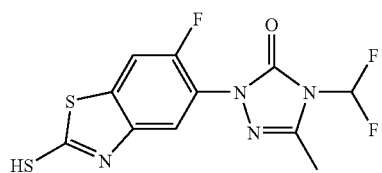

30 mL N,N-dimethylformamide was charged with 0.01 mol 1-(5-amino-4-bromo-2-fluorophenyl)-4-(difluoromethyl)-3-methyl-1H-1,2,4-triazol-5(4H)-one. The mixture was stirred until it became clear. Then, 0.02 mol potassium ethyl xanthogenate was added to the mixture in two portions. The mixture was refluxed at 140° C. for 5 h, cooled, and poured into 100 mL ice water slurry. Then, the mixture was acidified with 6 mol/L hydrochloric acid, and a large amount of solids crushed out. The title compound was obtained in a 73% yield as a white solid after filtration.

M.p. 248-250° C.

Anal. Calcd for $C_{11}H_7F_3N_4OS_2$: C, 39.76; H, 2.12; N, 16.86; S, 19.30. Found: C, 39.56; H, 2.16; N, 17.00; S, 19.42.

$^1$H NMR(CDCl$_3$, δ/ppm): 2.508 (s, 3H, CH$_3$), 4.581 (s, 2H, CH$_2$), 7.377-7.662 (t, 1H, CH, J=58 Hz), 7.442-7.912 (m, 2H, ArH), 13.990 (s, 1H, SH).

Example 3

Preparation of 1-(6-bromo-2-mercaptobenzo[d]thiazol-5-yl)-4-(difluoromethyl)-3-methyl-1H-1,2,4-triazol-5(4H)-one

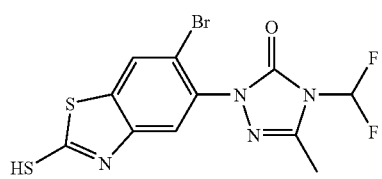

30 mL N,N-dimethylformamide was charged with 0.01 mol 1-(5-amino-2-bromo-4-fluorophenyl)-4-(difluoromethyl)-3-methyl-1H-1,2,4-triazol-5(4H)-one. The mixture was stirred until it became clear. Then, 0.02 mol potassium ethyl xanthogenate was added to the mixture in two portions. The mixture was refluxed at 140° C. for 7 h, cooled, and poured into 100 mL ice water slurry. Then, the mixture was acidified with 6 mol/L hydrochloric acid, and a large amount of solids crushed out. The title compound was obtained in a 48% yield as a white solid after filtration.

M.p. 254-256° C.

Anal. Calcd for $C_{11}H_7BrF_2N_4OS_2$: C, 33.60; H, 1.79; N, 14.25; S, 16.31. Found: C, 33.94; H, 2.11; N, 13.72; S, 15.24.

$^1$H NMR (CDCl$_3$, δ/ppm): 2.527 (s, 3H, CH$_3$), 6.972-7.262 (t, 1H, CH, J=58 Hz), 7.152 (s, 1H, 5-ArH), 7.691 (s, 1H, 2-ArH), 11.045 (s, 1H, SH).

Example 4

Preparation of 1-(6-fluoro-2-mercaptobenzo[d]thiazol-5-yl)-3,4-dimethyl-1H-1,2,4-triazol-5(4H)-one

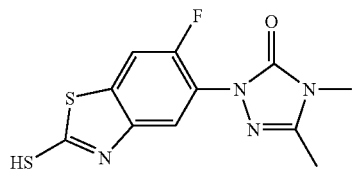

30 mL N,N-dimethylformamide was charged with 0.01 mol 1-(5-amino-4-bromo-2-fluorophenyl)-3,4-dimethyl-1H-1,2,4-triazol-5(4H)-one. The mixture was stirred until it became clear. 0.02 mol potassium ethyl xanthogenate was added to the mixture in two portions. The mixture was refluxed at 140° C. for 6 h, cooled, and poured into 100 mL ice water slurry. The mixture was acidified with 6 mol/L hydrochloric acid, and a large amount of solid materials crushed out. The title compound was obtained in a 75% yield as a white solid after filtration.

M.p. 299-301° C.

Anal. Calcd for $C_{11}H_9FN_4OS_2$: C, 44.58; H, 3.03; N, 18.91; S, 21.64. Found: C, 44.62; H, 2.83; N, 18.67; S, 21.39.

$^1$H NMR (CDCl$_3$, δ/ppm): 2.357 (s, 3H, CH$_3$), 3.400 (s, 3H, NCH$_3$), 7.301-7.470 (m, 2H, Ar), 11.215 (s, 1H, SH).

Example 5

Preparation of Ethyl 1-1-{6-chloro-5-[4-difluoromethyl-3-methyl-5-oxo-4,5-dihydro-1,2,4-triazol-1-yl]benzo[d]thiazol-2-ylthio}propanoate

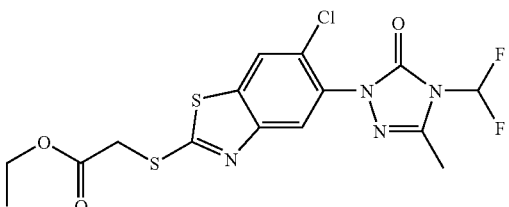

Water (5 mL) was charged with 0.0012 mol sodium hydroxide and with 0.001 mol 1-(6-chloro-2-mercaptobenzo[d]thiazol-5-yl)-4-(difluoromethyl)-3-methyl-1H-1,2,4-triazol-5(4H)-one. The mixture was stirred until it became clear. 0.0011 mol ethyl 2-bromoacetate dissolved in 1 mL of N,N-dimethylformamide were added to the mixture. The mixture was stirred at room temperature for 6 h, and thereafter 10 mL of water were added. The title compound was obtained in a 69% yield as a white solid after filtration.

M.p. 86-87° C.

Anal. Calcd for C$_{15}$H$_{13}$ClF$_2$N$_4$O$_3$S$_2$: C, 41.43; H, 3.01; N, 12.88; S, 14.75. Found: C, 41.39; H, 2.99; N, 12.91; S, 14.81.

$^1$H NMR (CDCl$_3$, δ/ppm): 1.274-1.310 (t, 3H, CH$_3$, J=7.2 Hz), 2.501 (s, 3H, CH$_3$), 4.161 (s, 2H, CH$_2$), 4.218-4.272 (q, 2H, CH$_2$, J=7.2 Hz), 6.936-7.227 (t, 1H, CH, J=58 Hz), 7.905 (s, 2H, ArH).

Example 6

Preparation of Ethyl 1-{5-[4-difluoromethyl-3-methyl-5-oxo-4,5-dihydro-1,2,4-triazol-1-yl]-6-fluoro benzo[d]thiazol-2-ylthio}acetate

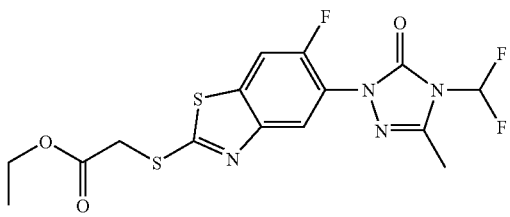

Water (5 mL) was charged with 0.0012 mol sodium hydroxide and with 0.001 mol 1-(6-fluoro-2-mercaptobenzo[d]thiazol-5-yl)-4-(difluoromethyl)-3-methyl-1H-1,2,4-triazol-5(4H)-one. The mixture was stirred until it became clear. 0.0011 mol ethyl 2-bromoacetate dissolved in 1 mL of N,N-dimethylformamide were added to the mixture. The mixture was stirred at room temperature for 6 h, and thereafter 10 mL of water were added. The title compound was obtained in an 84% yield as a white solid after filtration.

M.p. 91-93° C.

Anal. Calcd for C$_{15}$H$_{13}$F$_3$N$_4$O$_3$S$_2$: C, 43.06; H, 3.13; N, 13.39; S, 15.33. Found: C, 43.10; H, 3.19; N, 13.38; S, 15.46.

$^1$H NMR (CDCl$_3$, δ/ppm): 1.065-1.101 (t, 3H, CH$_3$, J=7.2 Hz), 1.831-1.886 (m, 2H, CH$_2$), 2.497 (s, 3H, CH$_3$), 3.308-3.345 (t, 2H, CH$_2$, J=7.2 Hz), 6.937-7.228 (t, 1H, CH, J=58 Hz), 7.584-7.946 (m, 2H, ArH).

Example 7

Preparation of 1-(2-(benzylsulfinyl)-6-fluorobenzo[d]thiazol-5-yl)-3,4-dimethyl-1H-1,2,4-triazol-5(4H)-one

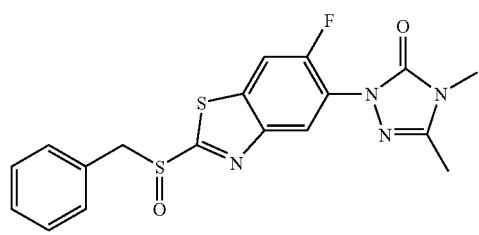

10 mL of dichloromethane was charged with 0.001 mol 1-(2-(benzylthio)-6-fluorobenzo[d]thiazol-5-yl)-3,4-dimethyl-1H-1,2,4-triazol-5(4H)-one. The mixture was stirred for 10 mins and then 0.0011 mol m-chloroperoxybenzoic acid (MCPBA) were added. After stirring at room temperature for 2 hours, the mixture was poured into 30 mL of water, extracted with 15 mL dichloromethane twice. Organic phases were combined and dried over anhydrous sodium sulfate. Filtration and removal of solvent under vacuum gave the title compound as a white solid in a 91% yield.

M.p. 162-164° C.

Anal. Calcd for C$_{18}$H$_{15}$FN$_4$O$_2$S$_2$: C, 53.72; H, 3.76; N, 13.92; S, 15.93. Found: C, 53.47; H, 3.53; N, 13.57; S, 15.44.

$^1$H NMR (CDCl$_3$, δ/ppm): 2.365 (s, 3H, CH$_3$), 3.366 (s, 3H, NCH$_3$), 4.313-4.539 (m, 2H, CH2, J=13.2 Hz), 7.101-7.319 (m, 5H, ArH), 7.740-7.762 (d, 1H, ArH, J=8.8 Hz), 8.225-8.241 (d, 1H, ArH, J=6.4 Hz).

Example 8

Preparation of 1-(6-fluoro-2-(methylsulfinyl)benzo[d]thiazol-5-yl)-3,4-dimethyl-1H-1,2,4-triazol-5(4H)-one

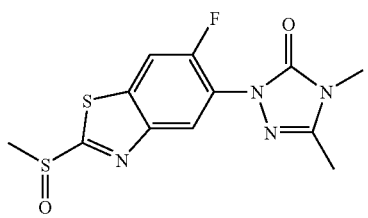

10 mL dichloromethane was charged with 0.001 mol 1-(6-fluoro-2-(methylthio)benzo[d]thiazol-5-yl)-3,4-dimethyl-1H-1,2,4-triazol-5(4H)-one. The mixture was stirred for 10 mins and then 0.0011 mol m-chloroperoxybenzoic acid (MCPBA) were added. After stirring at room temperature for 2 hours, the mixture was poured into 30 mL of water, extracted with 15 mL dichloromethane twice. Organic phases were combined and dried over anhydrous sodium sulfate. Filtration and removal of solvent under vacuum gave the title compound as a white solid in a 93% yield.

M.p. 199-201° C.

Anal. Calcd for C$_{12}$H$_{11}$FN$_4$O$_2$S$_2$: C, 44.16; H, 3.40; N, 17.17; S, 19.65. Found: C, 44.06; H, 3.06; N, 16.82; S, 19.46.

$^1$H NMR (CDCl$_3$, δ/ppm): 2.351 (s, 3H, CH$_3$), 3.090 (s, 3H, SCH$_3$), 3.353 (s, 3H, NCH$_3$), 7.838-7.861 (d, 1H, ArH, J=9.2 Hz), 8.204-8.222 (d, 1H, ArH, J=7.2 Hz).

Example 9

Preparation of 1-(2-(2-chlorobenzylsulfonyl)-6-chlorobenzo[d]thiazol-5-yl)-4-(difluoromethyl)-3-methyl-1H-1,2,4-triazol-5(4H)-one

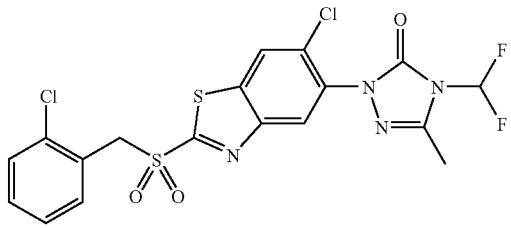

10 mL dichloromethane was charged with 0.001 mol 1-(2-(2-chlorobenzylthio)-6-chlorobenzo[d]thiazol-5-yl)-4-(difluoromethyl)-3-methyl-1H-1,2,4-triazol-5(4H)-one. The mixture was stirred for 10 mins and then 0.002 mol m-chloroperoxybenzoic acid (MCPBA) were added. After stirring at room temperature for 4 hours, the mixture was poured into 30 mL of water, then extracted with 15 mL dichloromethane twice. Organic phases were combined and dried over anhydrous sodium sulfate. Filtration and removal of solvent under vacuum gave the title compound as a white solid in a 90% yield.

M.p. 196-198° C.

Anal. Calcd for $C_{18}H_{12}Cl_2F_2N_4O_3S_2$: C, 42.87; H, 2.39; N, 11.09; S, 12.69. Found: C, 42.53; H, 2.43; N, 10.82; S, 13.11.

$^1$H NMR (CDCl$_3$, δ/ppm): 2.534 (s, 3H, CH$_3$), 4.985 (s, 2H, CH$_2$), 6.959-7.250 (t, 1H, CHF$_2$), 7.267-7.413 (m, 4H, ArH), 8.146-8.330 (d, 2H, ArH).

Example 10

Preparation of 1-(6-fluoro-2-(propylsulfonyl)benzo[d]thiazol-5-yl)-3,4-dimethyl-1H-1,2,4-triazol-5(4H)-one

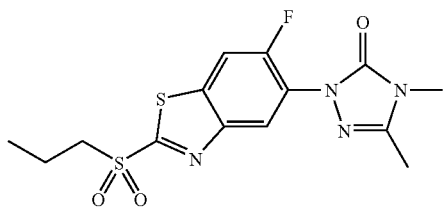

10 mL dichloromethane solution was charged with 0.001 mol 1-(6-fluoro-2-(propylthio)benzo[d]thiazol-5-yl)-3,4-dimethyl-1H-1,2,4-triazol-5(4H)-one. The mixture was stirred for 10 mins and then 0.002 mol m-chloroperoxybenzoic acid (MCPBA) were added. After stirring at room temperature for 4 hours, the mixture was poured into 30 mL of water, extracted with 15 mL dichloromethane twice. Organic phases were combined and dried over anhydrous sodium sulfate. Filtration and removal of solvent under vacuum gave the title compound as a white solid in a 95% yield.

M.p. 196-198° C.

Anal. Calcd for $C_{14}H_{15}FN_4OS_2$: C, 45.39; H, 4.08; N, 15.13; S, 17.31. Found: C, 45.44; H, 3.93; N, 14.91; S, 17.73.

$^1$H NMR (CDCl$_3$, δ/ppm): 1.062-1.100 (s, 3H, CH$_2$CH$_3$), 1.879-1.937 (s, 2H, CH$_2$CH$_3$), 2.357 (s, 3H, CH$_3$), 3.357 (s, 3H, NCH$_3$), 3.475-3.515 (m, 2H, SCH$_2$), 7.839-7.862 (d, 1H, ArH, J=9.2 Hz), 8.366-8.383 (d, 1H, ArH, J=6.8)

Other derivatives taught herein were prepared using the above methods. A selection of synthesized compounds according to the invention is listed in Table 1.

TABLE 1

2-(Benzo[d]thiazol-5-yl)-2H-1,2,4-triazol-3(4H)-one derivatives

| No. | X | R$^1$ | R$^2$ | R$^3$ | n |
|---|---|---|---|---|---|
| 1 | Cl | Het1 | CHF$_2$ | CH$_3$ | 0 |
| 2 | Cl | C$_6$H$_5$CH$_2$ | CHF$_2$ | CH$_3$ | 0 |
| 3 | Cl | 2-Cl—C$_6$H$_5$CH$_2$ | CHF$_2$ | CH$_3$ | 0 |
| 4 | Cl | 3-Cl—C$_6$H$_5$CH$_2$ | CHF$_2$ | CH$_3$ | 0 |
| 5 | Cl | 4-Cl—C$_6$H$_5$CH$_2$ | CHF$_2$ | CH$_3$ | 0 |
| 6 | Cl | 4-Br—C$_6$H$_5$CH$_2$ | CHF$_2$ | CH$_3$ | 0 |
| 7 | Cl | 3-F—C$_6$H$_5$CH$_2$ | CHF$_2$ | CH$_3$ | 0 |
| 8 | Cl | 2,4-2F—C$_6$H$_5$CH$_2$ | CHF$_2$ | CH$_3$ | 0 |
| 9 | Cl | 2,6-2F—C$_6$H$_5$CH$_2$ | CHF$_2$ | CH$_3$ | 0 |
| 10 | F | Het2 | CHF$_2$ | CH$_3$ | 0 |
| 11 | F | C$_6$H$_5$CH$_2$ | CHF$_2$ | CH$_3$ | 0 |
| 12 | F | 2,4-2F—C$_6$H$_5$CH$_2$ | CHF$_2$ | CH$_3$ | 0 |
| 13 | F | 3-NO$_2$—C$_6$H$_5$CH$_2$ | CHF$_2$ | CH$_3$ | 0 |
| 14 | F | 2-CH$_3$—C$_6$H$_5$CH$_2$ | CHF$_2$ | CH$_3$ | 0 |
| 15 | F | 4-CH$_3$—C$_6$H$_5$CH$_2$ | CHF$_2$ | CH$_3$ | 0 |
| 16 | F | 2-NO$_2$-5-CH$_3$—C$_6$H$_5$CH$_2$ | CHF$_2$ | CH$_3$ | 0 |
| 17 | F | 3-OCH$_3$—C$_6$H$_5$CH$_2$ | CHF$_2$ | CH$_3$ | 0 |
| 18 | F | 2-F—C$_6$H$_5$CH$_2$ | CHF$_2$ | CH$_3$ | 0 |
| 19 | F | 3-F—C$_6$H$_5$CH$_2$ | CHF$_2$ | CH$_3$ | 0 |
| 20 | F | 4-F—C$_6$H$_5$CH$_2$ | CHF$_2$ | CH$_3$ | 0 |
| 21 | F | 3-Br—C$_6$H$_5$CH$_2$ | CHF$_2$ | CH$_3$ | 0 |
| 22 | F | 2-F-4-Br—C$_6$H$_5$CH$_2$ | CHF$_2$ | CH$_3$ | 0 |
| 23 | F | 3-Cl—C$_6$H$_5$CH$_2$ | CHF$_2$ | CH$_3$ | 0 |
| 24 | F | 2-Cl—C$_6$H$_5$CH$_2$ | CHF$_2$ | CH$_3$ | 0 |
| 25 | Br | 4-Cl—C$_6$H$_5$CH$_2$ | CHF$_2$ | CH$_3$ | 0 |
| 26 | Br | 4-Br—C$_6$H$_5$CH$_2$ | CHF$_2$ | CH$_3$ | 0 |
| 27 | Br | 4-F—C$_6$H$_5$CH$_2$ | CHF$_2$ | CH$_3$ | 0 |
| 28 | Br | Het3 | CHF$_2$ | CH$_3$ | 0 |
| 29 | F | Het4 | CHF$_2$ | CH$_3$ | 0 |
| 30 | F | C$_6$H$_5$CH$_2$ | CH$_3$ | CH$_3$ | 0 |
| 31 | F | CH$_3$ | CH$_3$ | CH$_3$ | 0 |
| 32 | F | 3-Cl—C$_6$H$_5$CH$_2$ | CH$_3$ | CH$_3$ | 0 |
| 33 | F | C$_3$H$_7$ | CH$_3$ | CH$_3$ | 0 |
| 34 | F | C$_6$H$_5$CH$_2$ | CH$_3$ | CH$_3$ | 2 |
| 35 | F | CH$_3$ | CH$_3$ | CH$_3$ | 2 |
| 36 | F | 3-Cl—C$_6$H$_5$CH$_2$ | CH$_3$ | CH$_3$ | 2 |
| 37 | Cl | C$_6$H$_5$CH$_2$ | CHF$_2$ | CH$_3$ | 2 |
| 38 | Cl | 2,6-2F—C$_6$H$_5$CH$_2$ | CHF$_2$ | CH$_3$ | 2 |
| 39 | Cl | 2-Cl—C$_6$H$_5$CH$_2$ | CHF$_2$ | CH$_3$ | 2 |
| 40 | Cl | 3-Cl—C$_6$H$_5$CH$_2$ | CHF$_2$ | CH$_3$ | 2 |
| 41 | Cl | 4-Cl—C$_6$H$_5$CH$_2$ | CHF$_2$ | CH$_3$ | 2 |
| 42 | Cl | 4-Br—C$_6$H$_5$CH$_2$ | CHF$_2$ | CH$_3$ | 2 |
| 43 | F | 2-CH$_3$—C$_6$H$_5$CH$_2$ | CHF$_2$ | CH$_3$ | 2 |
| 44 | Cl | 3-F—C$_6$H$_5$CH$_2$ | CHF$_2$ | CH$_3$ | 2 |
| 45 | Cl | 2,4-2F—C$_6$H$_5$CH$_2$ | CHF$_2$ | CH$_3$ | 2 |
| 46 | F | 2-NO$_2$-5-CH$_3$—C$_6$H$_5$CH$_2$ | CHF$_2$ | CH$_3$ | 2 |
| 47 | F | 4-CH$_3$—C$_6$H$_5$CH$_2$ | CHF$_2$ | CH$_3$ | 2 |
| 48 | F | C$_3$H$_7$ | CH$_3$ | CH$_3$ | 2 |
| 49 | F | 2,4-2F—C$_6$H$_5$CH$_2$ | CHF$_2$ | CH$_3$ | 2 |
| 50 | F | 3-NO$_2$—C$_6$H$_5$CH$_2$ | CHF$_2$ | CH$_3$ | 2 |
| 51 | F | C$_6$H$_5$CH$_2$ | CHF$_2$ | CH$_3$ | 2 |
| 52 | F | 2-F—C$_6$H$_5$CH$_2$ | CHF$_2$ | CH$_3$ | 2 |
| 53 | F | 3-Cl—C$_6$H$_5$CH$_2$ | CHF$_2$ | CH$_3$ | 2 |
| 54 | Br | CH$_2$CO$_2$C$_2$H$_5$ | CHF$_2$ | CH$_3$ | 2 |
| 55 | F | C$_6$H$_{13}$ | CHF$_2$ | CH$_3$ | 2 |
| 56 | F | C$_2$H$_5$ | CHF$_2$ | CH$_3$ | 2 |
| 57 | Cl | C$_6$H$_{13}$ | CHF$_2$ | CH$_3$ | 2 |
| 58 | Cl | C$_2$H$_5$ | CHF$_2$ | CH$_3$ | 2 |
| 59 | Br | CH$_3$CHCO$_2$C$_2$H$_5$ | CHF$_2$ | CH$_3$ | 2 |
| 60 | Br | CH$_2$=CHCH$_2$ | CHF$_2$ | CH$_3$ | 2 |
| 61 | F | CH$_3$CHCO$_2$C$_2$H$_5$ | CHF$_2$ | CH$_3$ | 2 |
| 62 | F | CH$_3$ | CHF$_2$ | CH$_3$ | 2 |
| 63 | F | C$_4$H$_9$ | CHF$_2$ | CH$_3$ | 2 |
| 64 | F | n-C$_3$H$_7$ | CHF$_2$ | CH$_3$ | 2 |
| 65 | F | CH$_2$CO$_2$C$_2$H$_5$ | CHF$_2$ | CH$_3$ | 2 |
| 66 | F | CH$_2$=CHCH$_2$ | CHF$_2$ | CH$_3$ | 2 |
| 67 | Cl | CH$_3$CHCO$_2$C$_2$H$_5$ | CHF$_2$ | CH$_3$ | 2 |
| 68 | Cl | CH$_3$ | CHF$_2$ | CH$_3$ | 2 |
| 69 | Cl | C$_4$H$_9$ | CHF$_2$ | CH$_3$ | 2 |
| 70 | Cl | CH$_2$CO$_2$C$_2$H$_5$ | CHF$_2$ | CH$_3$ | 2 |
| 71 | Cl | CH$_2$=CHCH$_2$ | CHF$_2$ | CH$_3$ | 2 |
| 72 | Cl | n-C$_3$H$_7$ | CHF$_2$ | CH$_3$ | 2 |
| 73 | F | Het5 | CHF$_2$ | CH$_3$ | 0 |
| 74 | F | Het6 | CHF$_2$ | CH$_3$ | 0 |
| 75 | F | Het7 | CHF$_2$ | CH$_3$ | 0 |
| 76 | Cl | C$_2$H$_4$OCH$_3$ | CHF$_2$ | CH$_3$ | 0 |
| 77 | Cl | C$_2$H$_4$Cl | CHF$_2$ | CH$_3$ | 0 |
| 78 | Cl | C$_2$H$_4$OC$_2$H$_5$ | CHF$_2$ | CH$_3$ | 0 |
| 79 | Br | CH$_3$ | CHF$_2$ | CH$_3$ | 0 |
| 80 | Br | C$_2$H$_5$ | CHF$_2$ | CH$_3$ | 0 |
| 81 | Br | n-C$_3$H$_7$ | CHF$_2$ | CH$_3$ | 0 |
| 82 | Br | CH$_2$CO$_2$C$_2$H$_5$ | CHF$_2$ | CH$_3$ | 0 |
| 83 | F | C$_6$H$_{13}$ | CHF$_2$ | CH$_3$ | 0 |

TABLE 1-continued

2-(Benzo[d]thiazol-5-yl)-2H-1,2,4-triazol-3(4H)-one derivatives

| No. | X  | R¹ | R² | R³ | n |
|-----|----|----|----|----|---|
| 84  | F  | $C_2H_5$ | $CHF_2$ | $CH_3$ | 0 |
| 85  | Cl | $C_6H_{13}$ | $CHF_2$ | $CH_3$ | 0 |
| 86  | Cl | $C_2H_5$ | $CHF_2$ | $CH_3$ | 0 |
| 87  | Br | $CH_3CHCO_2C_2H_5$ | $CHF_2$ | $CH_3$ | 0 |
| 88  | Br | $CH_2=CHCH_2$ | $CHF_2$ | $CH_3$ | 0 |
| 89  | F  | $CH_3CHCO_2C_2H_5$ | $CHF_2$ | $CH_3$ | 0 |
| 90  | F  | $CH_3$ | $CHF_2$ | $CH_3$ | 0 |
| 91  | F  | $C_4H_9$ | $CHF_2$ | $CH_3$ | 0 |
| 92  | F  | $C_3H_7$ | $CHF_2$ | $CH_3$ | 0 |
| 93  | F  | $CH_2CO_2C_2H_5$ | $CHF_2$ | $CH_3$ | 0 |
| 94  | F  | $CH_2=CHCH_2$ | $CHF_2$ | $CH_3$ | 0 |
| 95  | Cl | $CH_3CHCO_2C_2H_5$ | $CHF_2$ | $CH_3$ | 0 |
| 96  | Cl | $CH_3$ | $CHF_2$ | $CH_3$ | 0 |
| 97  | Cl | $C_4H_9$ | $CHF_2$ | $CH_3$ | 0 |
| 98  | Cl | $CH_2CO_2C_2H_5$ | $CHF_2$ | $CH_3$ | 0 |
| 99  | Cl | $CH_2=CHCH_2$ | $CHF_2$ | $CH_3$ | 0 |
| 100 | Cl | $C_3H_7$ | $CHF_2$ | $CH_3$ | 0 |
| 101 | F  | $C_6H_5CH_2$ | $CH_3$ | $CH_3$ | 1 |
| 102 | F  | $CH_3$ | $CH_3$ | $CH_3$ | 1 |
| 103 | F  | 3-Cl—$C_6H_5CH_2$ | $CH_3$ | $CH_3$ | 1 |
| 104 | F  | 2-$CH_3$—$C_6H_5CH_2$ | $CHF_2$ | $CH_3$ | 1 |
| 105 | F  | 4-$CH_3$—$C_6H_5CH_2$ | $CHF_2$ | $CH_3$ | 1 |
| 106 | F  | 2-$NO_2$-5-$CH_3$—$C_6H_5CH_2$ | $CHF_2$ | $CH_3$ | 1 |
| 107 | Cl | 3-Cl—$C_6H_5CH_2$ | $CHF_2$ | $CH_3$ | 1 |
| 108 | Br | $CH_3$ | $CHF_2$ | $CH_3$ | 1 |
| 109 | Br | $C_2H_5$ | $CHF_2$ | $CH_3$ | 1 |
| 110 | Br | n-$C_3H_7$ | $CHF_2$ | $CH_3$ | 1 |
| 111 | Br | $CH_2CO_2C_2H_5$ | $CHF_2$ | $CH_3$ | 1 |
| 112 | F  | $C_6H_{13}$ | $CHF_2$ | $CH_3$ | 1 |
| 113 | F  | $C_2H_5$ | $CHF_2$ | $CH_3$ | 1 |
| 114 | Cl | $C_6H_{13}$ | $CHF_2$ | $CH_3$ | 1 |
| 115 | Cl | $C_2H_5$ | $CHF_2$ | $CH_3$ | 1 |
| 116 | Br | $CH_3CHCO_2C_2H_5$ | $CHF_2$ | $CH_3$ | 1 |
| 117 | Br | $CH_2=CHCH_2$ | $CHF_2$ | $CH_3$ | 1 |
| 118 | F  | $CH_3CHCO_2C_2H_5$ | $CHF_2$ | $CH_3$ | 1 |
| 119 | F  | $CH_3$ | $CHF_2$ | $CH_3$ | 1 |
| 120 | F  | $C_4H_9$ | $CHF_2$ | $CH_3$ | 1 |
| 121 | F  | $C_3H_7$ | $CHF_2$ | $CH_3$ | 1 |
| 122 | F  | $CH_2CO_2C_2H_5$ | $CHF_2$ | $CF_3$ | 0 |
| 123 | F  | $CH_2=CHCH_2$ | $CHF_2$ | $CF_3$ | 0 |
| 124 | Cl | $CH_3CHCO_2C_2H_5$ | $CHF_2$ | $CF_3$ | 0 |
| 125 | Cl | $CH_3$ | $CHF_2$ | $CF_3$ | 0 |
| 126 | Cl | $C_4H_9$ | $CHF_2$ | $CF_3$ | 0 |
| 127 | Br | $CH_2CO_2C_2H_5$ | $CHF_2$ | $CF_3$ | 0 |
| 128 | Br | $CH_2=CHCH_2$ | $CHF_2$ | $CF_3$ | 0 |
| 129 | Br | $C_3H_7$ | $CHF_2$ | $CF_3$ | 0 |
| 130 | F  | $CH2C\equiv CH$ | $CHF_2$ | $CH_3$ | 0 |

Abbreviations:

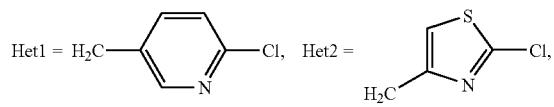

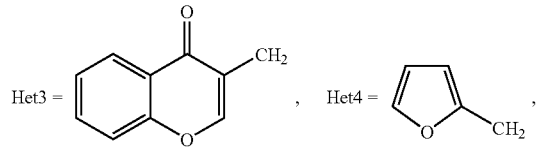

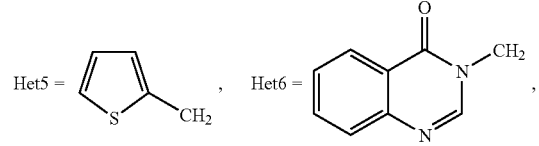

The following test of herbicidal activities illustrates that compounds represented by the general formula I possess significant herbicidal activities for barnyard grass, common crabgrass, green bristlegrass, mustard, amaranthus retroflexus and small goosefoot.

Example 11

Test of Herbicidal Activities (Greenhouse Pot Method)

Materials

Garden soil was collected from regions where no pesticide is used and mixed uniformly with mountain soil and organic humus soil at a volume ratio of 1:1:1.

Multiple flowerpots each having a diameter of 9.5 cm and a depth of 8 cm were filled with the soil mixture to 3/4 volume. After water was added to the soil and the soil was completely wet, seeds of three grass weeds and three broadleaf weeds were inserted into the flowerpots (10-15 seeds for each weed). After seeding, the seeds were covered with fine oil mixed with sand and having a thickness of 1-3 cm. After the soil absorbed enough water and became saturated, excess water at the bottom of the flowerpot was drained, and the seeds were placed in a greenhouse for growth.

The weeds were watered every day so as to keep relative humidity of the soil at approximately 80%, growing temperature of 15-30° C., and air humidity above 50%. As the grass weeds grew to a 2-leaf stage and the broadleaf weeds was in a leaf period, spraying operation before germination was performed on the stems and leafs. Planting before germination was performed before spraying. Soil processing was performed before the seeds of the weeds emerged.

Test Method

Six target weeds comprising three grass weeds: *Echinochloa crusgalli, Digiatria sanguinalis, Setaria viridis*, along with three broadleaf weeds: *Brassica juncea, Amaranthus retroflexus, Chenopodium album* were treated before/after germination using a so-called "greenhouse pot" method with a single dose. A treating dose was 300 g ai./h. The process was repeated three times, and a blank control was used.

A 3WPSHZ-500 type automatic spraying tower with a spraying area of 0.132 m², a spray volume of 10 mL, working pressure of 0.2 MPa, and a liquid volume of 40% of maximum was used. After treatment, the weeds were placed in a greenhouse at a temperature of 15-30° C. Reaction symptoms of the weeds were regularly observed, and 15 days later, five reaction levels were determined according to the following inhibition intervals: 90≦A≦100%; 80≦B<90%, 60≦C<80%; 50≦D<60%, E<50%.

TABLE 2

Herbicidal activity of compounds listed in Table 1

| No. | Echinochloa crusgalli | Digiatria sanguinalis | Setaria viridis | Brassica juncea | Amaranthus retroflexus | Chenopodium album |
|---|---|---|---|---|---|---|
| 1 | B | B | D | B | A | C |
| 2 | C | C | B | B | A | E |
| 3 | E | C | E | C | B | E |
| 4 | C | E | C | E | B | C |
| 5 | C | B | E | B | A | E |
| 6 | B | E | C | C | B | B |
| 7 | E | B | B | C | B | E |
| 8 | E | B | C | C | C | C |
| 9 | B | B | E | A | B | C |
| 10 | B | C | C | A | B | C |
| 11 | E | B | C | A | B | C |
| 12 | E | B | B | C | A | E |
| 13 | C | B | C | B | A | C |
| 14 | B | C | C | A | B | C |
| 15 | B | C | B | A | A | B |
| 16 | C | C | B | B | C | C |
| 17 | C | E | B | A | A | B |
| 18 | C | A | B | B | A | C |
| 19 | E | B | C | B | A | A |
| 20 | C | C | B | B | A | B |
| 21 | C | B | E | B | A | B |
| 22 | C | C | C | D | B | D |
| 23 | C | C | D | E | A | D |
| 24 | C | B | D | C | A | B |
| 25 | D | C | B | C | E | E |
| 26 | D | C | C | B | B | A |
| 27 | B | D | B | A | D | C |
| 28 | B | B | D | A | C | C |
| 29 | C | B | B | C | C | B |
| 30 | E | B | B | D | A | C |
| 31 | B | A | B | B | A | C |
| 32 | B | A | C | B | A | A |
| 33 | B | A | B | A | A | B |
| 34 | B | A | A | D | B | C |
| 35 | C | A | A | D | B | C |
| 36 | C | C | D | C | D | D |
| 37 | D | C | E | D | C | A |
| 38 | C | D | B | D | C | C |
| 39 | E | C | C | B | B | C |
| 40 | E | C | C | B | B | D |
| 41 | D | B | C | C | C | D |
| 42 | E | A | B | C | A | D |
| 43 | D | D | C | C | A | C |
| 44 | C | C | B | C | B | C |
| 45 | E | A | C | B | A | B |
| 46 | D | B | B | E | A | C |
| 47 | B | A | C | A | A | C |
| 48 | B | B | C | B | B | D |
| 49 | A | C | D | A | A | B |
| 50 | B | A | B | C | B | D |
| 51 | C | A | A | B | A | B |
| 52 | E | A | B | B | C | B |
| 53 | C | B | D | A | B | B |
| 54 | B | C | D | A | B | C |
| 55 | E | B | B | C | C | A |
| 56 | B | D | D | A | A | C |
| 57 | D | A | D | B | A | C |
| 58 | B | A | C | B | A | A |
| 59 | D | C | C | A | A | B |
| 60 | B | A | C | A | A | B |
| 61 | C | A | C | A | A | B |
| 62 | A | B | A | D | C | D |
| 63 | B | A | C | B | A | A |
| 64 | B | A | B | D | B | B |
| 65 | C | B | B | A | A | A |
| 66 | A | B | A | B | B | B |
| 67 | C | A | B | B | C | B |
| 68 | A | B | B | B | A | C |
| 69 | A | B | B | B | A | C |
| 70 | B | B | B | B | B | B |
| 71 | C | C | B | B | C | B |
| 72 | A | B | C | B | A | B |
| 73 | B | A | B | B | A | A |
| 74 | A | B | A | B | B | C |

TABLE 2-continued

Herbicidal activity of compounds listed in Table 1

| No. | Echinochloa crusgalli | Digiatria sanguinalis | Setaria viridis | Brassica juncea | Amaranthus retroflexus | Chenopodium album |
|---|---|---|---|---|---|---|
| 75 | C | B | A | C | A | B |
| 76 | A | A | B | C | A | C |
| 77 | A | B | A | B | A | A |
| 78 | C | A | A | D | A | B |
| 79 | B | A | B | B | B | C |
| 80 | A | B | A | A | A | E |
| 81 | B | D | B | A | A | B |
| 82 | A | A | A | B | A | C |
| 83 | B | D | A | C | A | A |
| 84 | A | A | B | C | B | A |
| 85 | B | A | A | B | B | B |
| 86 | A | A | A | A | A | B |
| 87 | B | B | A | A | B | B |
| 88 | B | A | D | A | A | B |
| 89 | A | A | A | B | B | C |
| 90 | B | A | A | A | A | A |
| 91 | A | A | A | A | A | C |
| 92 | B | B | C | A | A | E |
| 93 | A | A | B | A | A | A |
| 94 | A | A | A | B | B | B |
| 95 | A | A | A | D | A | B |
| 96 | B | B | C | B | B | B |
| 97 | B | C | C | B | B | B |
| 98 | A | A | A | A | A | B |
| 99 | A | B | B | B | B | C |
| 100 | B | B | C | A | A | A |
| 101 | B | C | C | D | C | B |
| 102 | E | D | C | C | B | A |
| 103 | E | B | B | D | A | A |
| 104 | C | C | C | A | A | A |
| 105 | D | C | B | B | B | B |
| 106 | D | D | B | B | D | A |
| 107 | B | B | D | A | A | B |
| 108 | A | B | B | A | B | E |
| 109 | A | B | B | A | B | A |
| 110 | A | B | C | B | B | B |
| 111 | A | C | C | B | A | E |
| 112 | B | A | B | C | B | B |
| 113 | B | C | C | A | B | D |
| 114 | B | A | B | A | A | A |
| 115 | C | B | B | A | B | D |
| 116 | D | C | B | A | B | B |
| 117 | C | B | E | C | C | B |
| 118 | D | C | C | D | A | B |
| 119 | E | C | C | E | B | B |
| 120 | D | B | B | A | C | B |
| 121 | E | C | D | C | D | A |
| 122 | C | E | E | E | E | E |
| 123 | D | B | B | D | A | A |
| 124 | D | E | A | B | B | B |
| 125 | B | B | C | C | A | B |
| 126 | B | A | C | A | B | B |
| 127 | C | B | D | B | B | B |
| 128 | A | C | D | A | A | B |
| 129 | A | A | C | C | A | A |
| 130 | B | C | A | D | A | B |

Note:
90 ≦ A ≦ 100%;
80 ≦ B < 90%,
60 ≦ C < 80%;
50 ≦ D < 60%,
E < 50%

The compounds of the invention, when used as an herbicide, can be mixed with other carriers or diluents that are allowed by plant protection laws. They can be formulates in various application forms, such as powders, wettable powders, granules, suspending agents, aqueous emulsions, and so on. In addition, the compound of the invention can be mixed with or used along with other herbicides.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A compound of formula I:

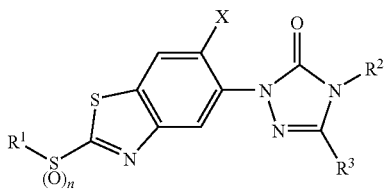

wherein
X represents F, Cl, or Br;
n is 0, 1 or 2;
$R^1$ represents alkyl, substituted alkyl, haloalkyl, alkenyl, alkynyl, alkynylalkyl, carboxylic acid ester radical, dialkyl ether radical, benzyl, substituted benzyl, halobenzyl, or substituted aromatic heterocyclic methyl;
$R^2$ represents methyl or difluoromethyl;
$R^3$ represents methyl or trifluoromethyl.

2. A method for preparation of the compound of formula I of claim 1, comprising contacting a compound of formula II with a compound of formula III in the presence of a base:

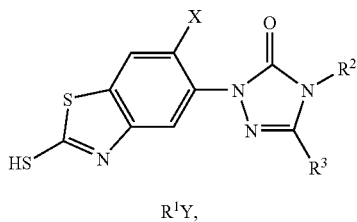

wherein
X represents F, Cl, or Br;
n is equal to 0;
$R^1$ represents alkyl, substituted alkyl, haloalkyl, alkenyl, alkynyl, alkynylalkyl, carboxylic acid ester radical, dialkyl ether radical, benzyl, substituted benzyl, halobenzyl, or substituted aromatic heterocyclic methyl;
$R^2$ represents methyl or difluoromethyl; and
$R^3$ represents methyl or trifluoromethyl.

3. The method of claim 2, wherein
molar ratio of the compound of formula II, to the compound of formula III, to the base is 1:1.1:1.2;
the base is sodium hydroxide;
a mixture of water and N,N-dimethylformamide at a volume ratio of 5:1 is used as solvent;
reaction temperature is about 25° C.; and
reaction time is between about 2 and about 6 hours.

4. A method for preparation of the compound of formula I of claim 1, comprising contacting a compound of formula I-1

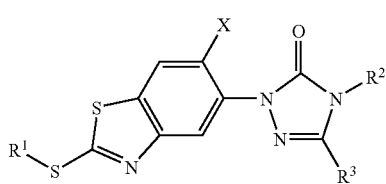

with m-chloroperoxybenzoic acid,
wherein
X represents F, Cl, or Br;
n is equal to 1 or 2;
$R^1$ represents alkyl, substituted alkyl, haloalkyl, alkenyl, alkynyl, alkynylalkyl, carboxylic acid ester radical, dialkyl ether radical, benzyl, substituted benzyl, halobenzyl, or substituted aromatic heterocyclic methyl;
$R^2$ represents methyl or difluoromethyl; and
$R^3$ represents methyl or trifluoromethyl.

5. The method of claim 4, wherein
molar ratio of the compound of formula I-1 to m-chloroperoxybenzoic acid is 1:1 or 1:2;
dichloromethane is used as solvent;
reaction temperature is 0-25° C.;
reaction time is between 2 hours and 4 hours;
when the molar ratio of the compound of formula I-1 to m-chloroperoxybenzoic acid is 1:1, n is equal to 1, and when the molar ratio of the compound of formula I-1 to m-chloroperoxybenzoic acid is 1:2, n is equal to 2.

6. A method for preparation of a compound of formula II

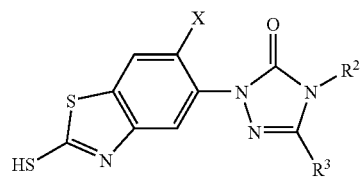

comprising contacting a compound of formula IV

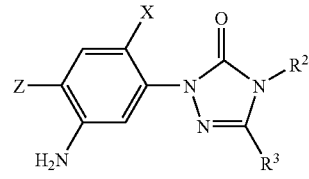

with potassium ethyl xanthogenate in N,N-dimethylformamide;
wherein
X represents F, Cl, or Br;
Z represents F, Cl, or Br;
$R^2$ represents methyl, or difluoromethyl; and
$R^3$ represents methyl, or trifluoromethyl.

7. The method of claim 6, wherein molar ratio of the compound of formula IV to potassium ethyl xanthogenate is 1:2;

N,N-dimethylformamide is used as solvent;

reaction temperature is 140° C.; and reaction time is between about 5 and about 7 hours.

8. A method for killing or inhibiting the growth of targeted plants comprising applying a diluted composition comprising the compound of formula I of claim 1 to the targeted plants.

9. The method of claim 8, wherein the compound of formula I is applied at a rate of 300 gai./h.

10. The method of claim 9, wherein the targeted plants are *Echinochloa crusgalli*.

11. The method of claim 9, wherein the targeted plants are *Digiatria sanguinalis*.

12. The method of claim 9, wherein the targeted plants are *Setaria viridis*.

13. The method of claim 9, wherein the targeted plants are *Brassica juncea*.

14. The method of claim 9, wherein the targeted plants are *Amaranthus retroflexus*.

15. The method of claim 9, wherein the targeted plants are *Chenopodium album*.

* * * * *